United States Patent
Picard et al.

[11] Patent Number: 6,020,366
[45] Date of Patent: Feb. 1, 2000

[54] BUTYRIC ACID MATRIX METALLOPROTEINASE INHIBITORS

[75] Inventors: Joseph Armand Picard, Canton; Drago Robert Sliskovic, Saline, both of Mich.

[73] Assignee: Warner-Lambert Company, Morris Plains, N.J.

[21] Appl. No.: 09/171,833

[22] PCT Filed: Jul. 16, 1997

[86] PCT No.: PCT/US97/12389

§ 371 Date: Oct. 27, 1998

§ 102(e) Date: Oct. 27, 1998

[87] PCT Pub. No.: WO98/06711

PCT Pub. Date: Feb. 19, 1998

Related U.S. Application Data

[60] Provisional application No. 60/024,025, Aug. 16, 1996.

[51] Int. Cl.$^7$ .......... A61K 31/34; C07D 307/91
[52] U.S. Cl. .......... 514/468; 549/460; 549/461
[58] Field of Search .......... 514/468; 549/460, 549/461

[56] References Cited

U.S. PATENT DOCUMENTS

| | | | |
|---|---|---|---|
| 4,528,282 | 7/1985 | Preston et al. | 514/19 |
| 5,665,764 | 9/1997 | Hupe et al. | 514/468 |

FOREIGN PATENT DOCUMENTS

| | | |
|---|---|---|
| 0084941 | 1/1983 | European Pat. Off. . |
| 9535275 | 12/1985 | WIPO . |
| 9209282 | 6/1992 | WIPO . |
| 9503271 | 2/1995 | WIPO . |
| 9600214 | 1/1996 | WIPO . |
| 9806711 | 2/1998 | WIPO . |

OTHER PUBLICATIONS

PCT International Search Report, PCT/US97/12389, 1998.
PCT International Preliminary Examination Report, PCT/US97/12389, 1998.

*Primary Examiner*—Joseph McKane
*Attorney, Agent, or Firm*—Charles W. Ashbrook

[57] ABSTRACT

Compounds of the formula

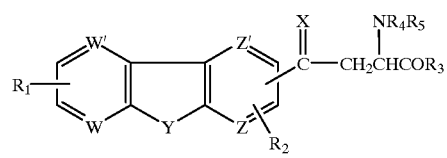

wherein $R_1$ and $R_2$ include hydrogen, alkyl, substituted alkyl, halo, and arylalkyl; $R_3$ is hydroxy, alkoxy, or hydroxyamino; X is O, S, or NOH; and $R_4$ and $R_5$ include hydrogen, alkyl, and aryl are useful for inhibiting matrix metalloproteinase enzymes in animals, and as such, prevent and treat diseases resulting from the breakdown of connective tissues.

42 Claims, No Drawings

BUTYRIC ACID MATRIX METALLOPROTEINASE INHIBITORS

This application claims benefit of Provisional Application 60/024,025 filed Aug. 16, 1996.

FIELD OF INVENTION

This invention relates to a group of butyric acid derivatives which inhibit matrix metalloproteinase enzymes and thus are useful for treating diseases resulting from tissue breakdown, such as arthritis and osteoporosis.

BACKGROUND OF THE INVENTION

Matrix metalloproteinases are naturally occurring enzymes found in most mammals and are associated with the breakdown of connective tissues. The class includes gelatinase A and B, stromelysin-1, fibroblast collagenase, neutrophil collagenase, matrilysin, and other forms of collagenase. These enzymes have been implicated with a number of diseases which result from breakdown of connective tissue, such as rheumatoid arthritis, osteoarthritis, osteoporosis, periodontitis, multiple sclerosis, gingivitis, corneal epidermal and gastric ulceration, atherosclerosis, neointimal proliferation which leads to restenosis and ischemic heart failure, and tumor metastasis. A method for preventing and treating these diseases is now recognized to be by inhibiting metalloproteinase enzymes, thereby curtailing and eliminating the breakdown of connective tissues that results in the disease states.

Several inhibitors of metalloproteinases have been identified. Many inhibitors are complex peptides, for instance as described by Chapman, et al., in *J. Med. Chem.*, 1993;36:4293–4301. Small peptide inhibitors are also known, for example as described in U.S. Pat. Nos. 4,599,361 and 5,270,326, as well as nonpeptides as in WO 95/35276.

The need continues for small molecular weight molecules which can be economically prepared and yet are effective inhibitors of metalloproteinases. We have now discovered a group of butyric acid derivatives which have exceptionally good inhibitory activity. An object of this invention is to provide such compounds, their pharmaceutical formulations, and a method for using them to treat diseases mediated by metalloproteinases.

SUMMARY OF THE INVENTION

This invention provides butyric acid derivatives which are inhibitors of matrix metalloproteinases. The invention compounds have Formula I

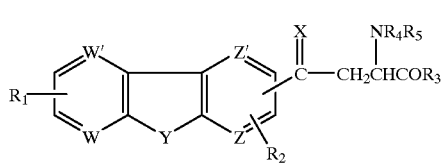

wherein:

X is O, $NOR_9$, S, OH, SH, or

$R_7$ and $R_{7a}$ independently are
hydrogen,
$C_1$–$C_{20}$ alkyl or substituted $C_1$–$C_{20}$ alkyl,
$(CH_2)_{0-6}$-aryl,
$(CH_2)_{0-6}$-heteroaryl, or
$(CH_2)_{0-6}$-cycloalkyl;
$R_1$ and $R_2$ independently are
hydrogen,
$C_1$–$C_{20}$ alkyl or substituted $C_1$–$C_{20}$ alkyl,
halo,
$NO_2$,
CN,
CHO,
$COR_6$,
$COOR_6$,
$SO_3R_6$,
$OR_6$,
$CONR_4R_5$,
$(CH_2)_{0-6}$-aryl,
$(CH_2)_{0-6}$-heteroaryl, or
$(CH_2)_{0-6}$-cycloalkyl;
$R_6$ is hydrogen,
$C_1$–$C_{20}$ alkyl or substituted $C_1$–$C_{20}$ alkyl;
aryl is phenyl or substituted phenyl;
$R_3$ is hydroxy,
O—$C_1$–$C_{20}$ alkyl or substituted O—$C_1$–$C_{20}$ alkyl,
O—$(CH_2)_{1-3}$ aryl, or
$NHOR_6$;
$R_4$ and $R_5$ independently are hydrogen,
$C_1$–$C_{20}$ alkyl or substituted $C_1$–$C_{20}$ alkyl,
$C_2$–$C_{20}$ alkenyl or substituted $C_2$–$C_{20}$ alkenyl,
$(CH_2)_{0-6}$-aryl,
$(CH_2)_{0-6}$-(O or S)-aryl,
$(CH_2)_{0-6}$-heteroaryl,
$(CH_2)_{0-6}$-(O or S)-heteroaryl;
or one of $R_4$ and $R_5$ is hydrogen and the other is:
$COR_8$,
$CSR_8$,
$CONR_8R_9$,
$CSNR_8R_9$,
$COOR_8$,
$COSR_8$,

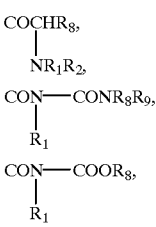

-continued

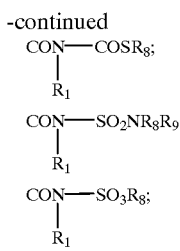

S(O)$_{1\,or\,2}$-C$_1$–C$_{20}$ alkyl or substituted alkyl,
S(O)$_{1\,or\,2}$-aryl
S(O)$_{1\,or\,2}$-heteroaryl, or
S(O)$_{1\,or\,2}$-cycloalkyl;
Y is

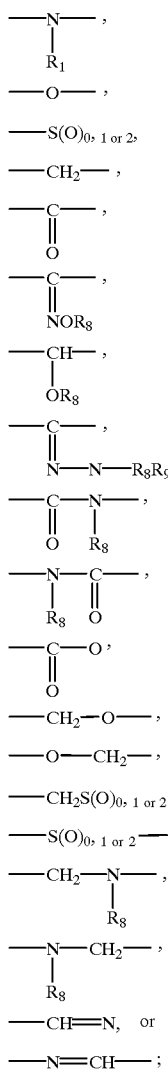

R$_8$ and R$_9$ independently are
hydrogen,
C$_1$–C$_{20}$ alkyl or substituted C$_1$–C$_{20}$ alkyl,
C$_2$–C$_{20}$ alkenyl or substituted C$_2$–C$_{20}$ alkenyl,
(CH$_2$)$_{0-6}$-(O or S)$_{0-1}$-aryl,
(CH$_2$)$_{0-6}$-(O or S)$_{0-1}$-heteroaryl, or
(CH$_2$)$_{0-6}$-(O or S)$_{0-1}$-cycloalkyl;

W, W$^1$, Z, and Z$^1$ independently are CR$_1$ or N;
the term

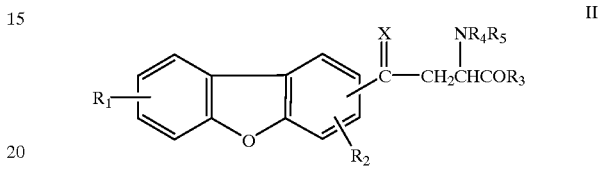

is a double bond when X is O, S, NOR$_9$, or
N-NR$_7$R$_{7a}$, and a single bond when X is OH or SH; and
the pharmaceutically acceptable salts, isomers,
stereoisomers, and solvates thereof.

Preferred compounds are defined by Formula II

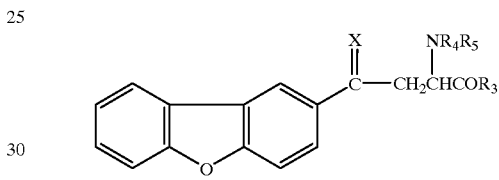

wherein R$_1$, R$_2$, R$_3$ R$_4$, R$_5$, and X are as defined above.
Further preferred compounds have the formula and especially preferred are those wherein X is O, and R$_3$ is
hydroxy. The most preferred compounds of the invention are
in this latter group where R$_4$ is hydrogen, and R$_5$ is COR$_8$,
COOR$_8$, or CONR$_8$R$_9$, where R$_8$ and R$_9$ are alkyl or
substituted alkyl, aryl or substituted aryl.

A further embodiment of this invention is a pharmaceutical formulation comprising a compound of Formula I admixed with a pharmaceutically acceptable carrier, excipient, or diluent therefor.

The invention additionally provides a method for inhibiting the hydrolytic activity of a matrix metalloproteinase enzyme comprising administering to a mammal an effective amount of a compound of Formula I. In a preferred embodiment, the invention is a method for inhibiting or treating multiple sclerosis, atherosclerotic plaque rupture, aortic aneurysms, heart failure, restenosis, periodontal disease, corneal ulceration, cancer metastasis, tumor angiogenesis, arthritis, and for wound healing.

DETAILED DESCRIPTION OF THE INVENTION

As used herein, the terms "C$_1$–C$_{20}$ alkyl" and "substituted C$_1$–C$_{20}$ alkyl" mean straight or branched aliphatic groups having from 1 to 20 carbon atoms, preferably 1 to 12, and typically 1 to 6, optionally substituted. Exemplary alkyl groups include methyl, ethyl, isopropyl, 1,1-dimethylheptyl, n-decyl, 1-n-butyl-2-isopropyldecyl, tert-butyl, isoundecyl, and the like. Substituted alkyl groups are the foregoing C$_1$–C$_{20}$ alkyl groups having one or more, typically from 1 to 3, substituent groups such as halo, hydroxy, C$_1$–C$_4$ alkoxy, thio, C$_1$–C$_4$ alkylthio, phenyl, alkylphenyl, phenoxy, alkylphenoxy, substituted phenyl or substituted phenoxy. Typical "substituted C$_1$–C$_{20}$ alkyl" groups thus include hydroxymethyl, n-butoxymethyl, chloromethyl, 1-(3-chlorophenoxy)ethyl-, 1,2,4-trifluorohexyl, 1-(phenoxymethyl)ethyl, 2-methoxydecyl, 4-methylthio-5-bromo-undecyl, 1-ethyl-3-phenylbutyl, 4-(3,4-dibromophenyl)-heptyl, pentadecafluoro-octyl, and 2,2,2-trifluoroethyl.

The terms "$C_2$–$C_{20}$ alkenyl" and "substituted $C_2$–$C_{20}$ alkenyl" mean the foregoing alkyl groups having one to four non-adjacent double bonds. Examples include prop-2-enyl, but-2-enyl, oct-2,4-dienyl, 2-phenylethenyl, 3-naphthyl-but-2-enyl, and 6-(2-pyridyl)-hex-3-enyl.

The term "halo" includes fluoro, bromo, chloro, and iodo. Several of the R groups in Formula I can be a group defined as "$COR_6$", "$COOR_6$", "$SO_3R_6$", and "$OR_6$", where $R_6$ is hydrogen, alkyl, or substituted alkyl as those terms are defined above. The $COR_6$ groups thus include formyl, acetyl, propionyl, pivaloyl, 3-hydroxybutyryl, undecanoyl, 4-n-butyl-5-chloro-6-methylthio-heptanoyl, 4-bromophenoxyacetyl, and 4-phenylpentanoyl. Typical $COOR_6$ groups include methoxycarbonyl, benzyloxycarbonyl, n-octyloxycarbonyl, 5-methoxy-6-thioheptyloxycarbonyl, and the like. Typical $SO_3R_6$ groups include methoxysulfonyl, 3-chlorobenzyloxysulfonyl, and 4-chlorobutyloxy-sulfonyl. The $OR_6$ groups include methoxy, tert-butoxy, benzyloxy, 4-nitrobenzyloxy, and the like.

The term "$CONR_4R_5$" means an aminocarbonyl substituent such as methylaminocarbonyl, benzylaminocarbonyl, diethylaminocarbonyl, 3-pyridylmethylaminocarbonyl, and the like.

The term "aryl" means a monocyclic or bicyclic aromatic hydrocarbyl group, for example, phenyl or naphthyl, optionally substituted with from one to five groups, typically one, two, or three, selected from halo, hydroxy, methylenedioxy, phenyl, nitro, cyano, $C_1$–$C_6$ alkyl, $C_1$–$C_6$ alkoxy, thio, $C_1$–$C_6$ alkylthio, amino, $C_1$–$C_6$ alkyl and dialkylamino, CHO, $COR_6$, $COOR_6$, $OR_6$, $SO_3R_6$, or $CONR_4R_5$. Typical $(CH_2)_{0-6}$-aryl groups thus include phenyl, 3-hydroxyphenyl, 2-methylphenyl, 4-chlorobenzyl, 3,4-methylenedioxyphenyl, 4-(2-methylthiophenyl)butyl, 2-(3-aminophenyl)ethyl, 6-(2-chloro-3-methylamino-4-formylphenyl)hexyl, naphthyl, 3-chloronaphthyl, and 2,4,6-trimethyl-naphthyl.

The term "$(CH_2)_{0-6}$-(O or S)-aryl" means the foregoing aryl groups bonded through oxygen or sulfur. Examples include phenoxymethyl, 2-phenylthioethyl, 1-naphthyloxymethyl, and 3-bromo-1-naphthylthiomethyl.

The term "$(CH_2)_{0-6}$-heteroaryl" means a heteroaryl group bonded directly or through from one to six methylene groups. The term "heteroaryl" means a monocyclic or fused bicyclic aromatic ring having from 4 to 12 carbon atoms and from 1 to 3 heteroatoms selected from O, S, or N. The heteroaryl group can be substituted with the same groups as indicated above for phenyl. Typical heteroaryl groups thus include pyridyl, 2- or 3-furanyl, 2- or 3-thienyl, 2- or 3-pyranyl, 2-, 4-, or 5-pyrimidinyl, 3- or 4-pyridazinyl, 2- or 3-morpholinyl, indolyl, 3-phenyl-2-pyridyl, benzoxazolyl, benzopyranyl, quinolinyl, quinoxalinyl, isoquinolinyl, and pyridopyrimidinyl. Substituted heteroaryl groups include 3-chlorothiophene, 3-hydroxyfuryl, and 3-nitromorpholine.

The term "$(CH_2)_{0-6}$-(O or S)-heteroaryl" means the foregoing heteroaryl groups bonded through oxygen or sulfur. Examples include 3-pyridyloxymethyl, 2-(2-pyranyl) oxyethyl, and 3-furanylthiomethyl.

The term "$(CH_2)_{0-6}$-(O or S)$_{0-1}$-cycloalkyl" means a cycloalkyl group bonded directly or through from one to six methylene groups, and optionally through oxygen or sulfur. "Cycloalkyl" means a monocyclic or bicyclic carbocyclic group having from three to ten carbon atoms, and optionally substituted with one, two, or three groups selected from halo, hydroxy, phenyl, nitro, cyano, $C_1$–$C_6$ alkyl, $C_1$–$C_6$ alkoxy, thio, $C_1$–$C_6$ alkylthio, amino, $C_1$–$C_6$ alkyl and dialkylamino, CHO, $COR_6$, $COOR_6$, $OR_6$, $SO_3R_6$, and $CONR_4R_5$. Typical cycloalkyl groups thus include cyclopropyl, cyclobutyl, cyclopentyl, cyclohexyl, 2-ethylcyclopentyl, 3,4-dichlorocyclohexyl, decalinyl, adamantyl, 3-aminocyclooctyl, and 2-phenylcyclohexyl.

$R_4$ and $R_5$ are nitrogen substituents and include hydrogen, alkyl and substituted alkyl, $(CH_2)_{0-6}$-(O or S)$_{0-1}$-aryl and $(CH_2)_{0-6}$-(O or S)$_{0-1}$-heteroaryl, as those terms are defined above. Preferred compounds of the invention are those wherein $R_4$ is hydrogen, and $R_5$ is other than hydrogen, especially $COR_8$, $CSR_8$, $CONR_8R_9$, $CSNR_8R_9$, $COOR_8$, $SO_2$-alkyl, $SO_2$-aryl, and $COSR_8$. These groups define compounds which are, respectively, amides, thioamides, ureas, thioureas, carbamates, sulfonamides, and thiocarbamates. Typical "$COR_8$" groups thus include formyl, acetyl, bromoacetyl, trifluoroacetyl, cyclobutylformyl, 3-nitropropionyl, 4-methoxycarbonylbutyryl, benzoyl, 4-phenylbenzoyl, phenoxyacetyl, 1-phenoxyethyl, 6-dimethylaminocarbonyl-octanoyl, and 4-phenyldecanoyl. Typical "$CSR_8$" groups include methylthiocarbonyl, ethylthiocarbonyl, and tert-butylthiocarbonyl. Examples of "$CONR_8R_9$" groups include aminocarbonyl, dimethylaminocarbonyl, dibenzylaminocarbonyl, and the like. The invention includes thioureas, i.e., compounds of Formula I where $R_4$ is hydrogen, and $R_5$ is

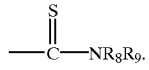

Typical of such $R_5$ groups are aminothiocarbonyl, diethylaminothiocarbonyl, and benzylaminothiocarbonyl. The invention also includes sulfonamides, for example when $R_5$ is —$SO_2$ alkyl or —SO2 aryl. Typical groups include isopropylsulfonyl, phenylsulfonyl, naphthylsulfonyl, and 4-chlorophenylsulfonyl.

$R_4$ and $R_5$ can include "$COOR_8$" and "$COSR_8$"; preferably, one of $R_4$ or $R_5$ is hydrogen. Such groups form carbamates and thiocarbamates, respectively. Typical $COOR_8$ groups include methoxycarbonyl, 3-hydroxybutoxycarbonyl, benzyloxycarbonyl, 2,4-dibromobenzyloxycarbonyl, 1-methoxy-2-phenyl-3-chloropropoxycarbonyl, and 10-methoxyundecyloxycarbonyl. Examples of "$COSR_8$" groups include methylthiocarbonyl, benzylthiocarbonyl, and the like.

Ideally, one of $R_4$ and $R_5$ is hydrogen when the other is

These groups are residues of naturally occurring as well as unnatural amino acids, for example, glycyl, alanyl, N-methylvalyl, N-benzylleucyl, N,N-dimethylphenylalanyl, threonyl, arginyl, glutamyl, lysyl, tyrosyl, 2-amino-6-chlorohexanoyl, 2-benzylamino-3,4-dimethoxyheptanoyl, and the like.

Ideally, $R_4$ is hydrogen when $R_5$ is a group having the formula

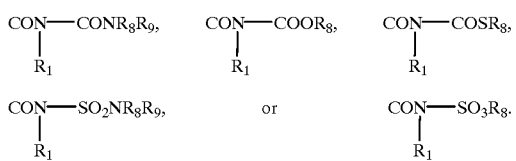
Examples of these groups include methylaminoformamidocarbonyl, ethoxyformamidocarbonyl, methylthioformamidocarbonyl, diethylaminosulfonylaminocarbonyl, and N-benzyloxysulfonyl-N-ethylaminocarbonyl.
Typical compounds provided by this invention are illustrated by the following general formulas:
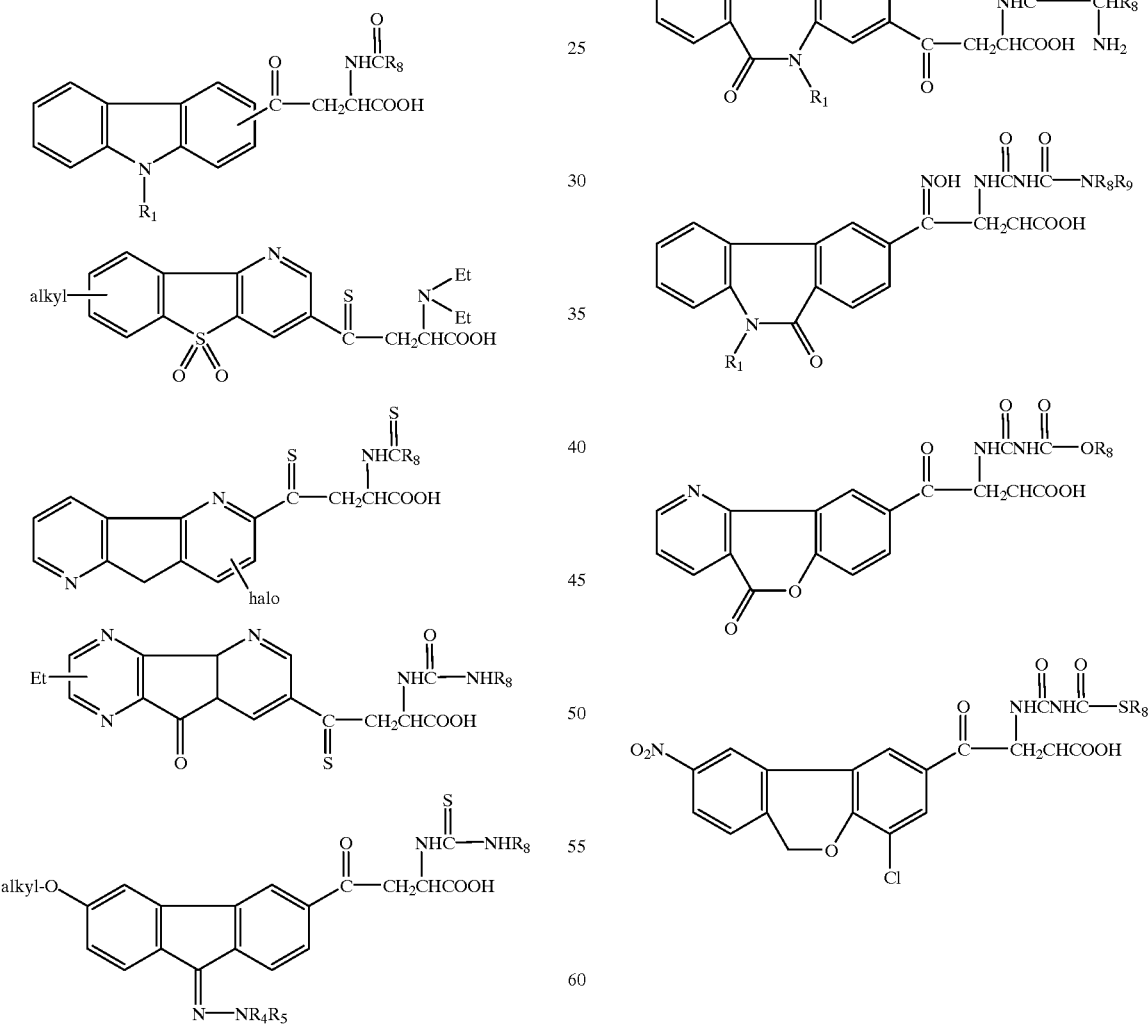

-continued

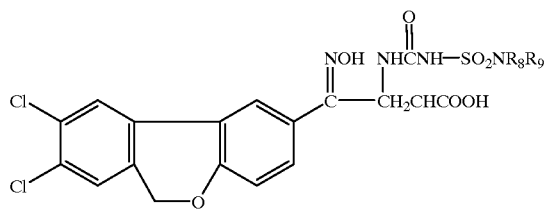

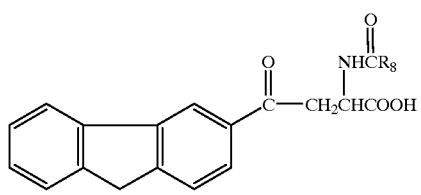

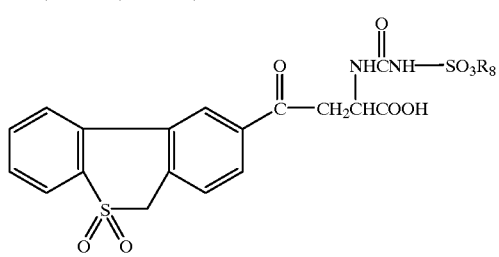

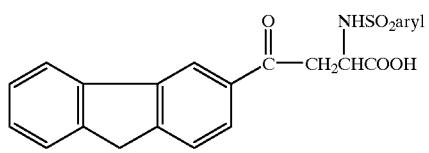

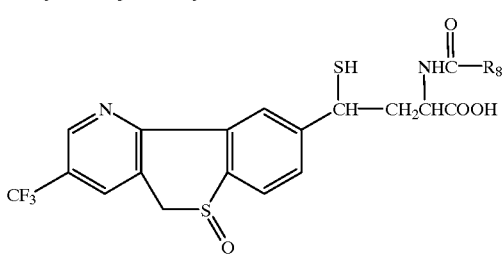

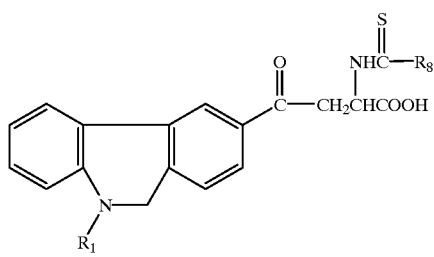

Especially preferred compounds are those illustrated below:

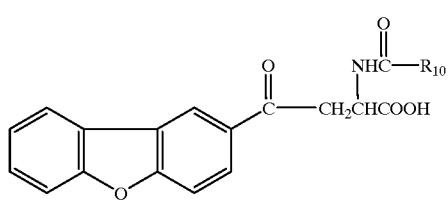

where $R_{10}$ is:

—$CF_3$,

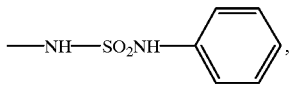

$C_1$–$C_{12}$ alkyl, or perfluoro-$C_1$–$C_{12}$ alkyl,

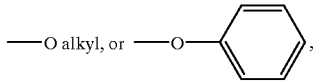

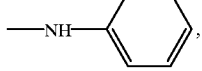

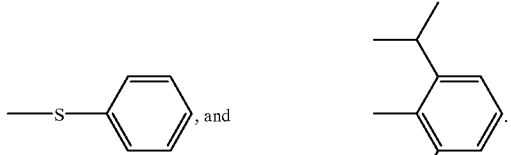

The invention compounds of Formula I are prepared by any of several procedures, utilizing reaction processes well-known to those having ordinary skill in the art of organic chemistry. A typical invention compound can be prepared by acylating a tricyclic reactant with an amino substituted butyryl acylating agent such as aspartic acid anhydride, or a butyryl agent of the formula

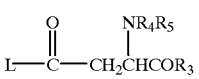

where L is a leaving group such as chloro or formyloxy, and $R_3$, $R_4$, and $R_5$ are as defined above. The acylation is conducted under Friedal Crafts conditions, for example utilizing aluminum chloride as a catalyst, and conducting the reaction in an organic solvent, preferably a halogenated hydrocarbon such as dichloromethane or chloroform. A preferred process comprises reacting a tricyclic starting material with an N-substituted D- or L-aspartic acid anhydride according to the following general scheme:

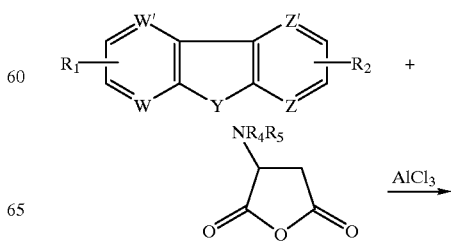

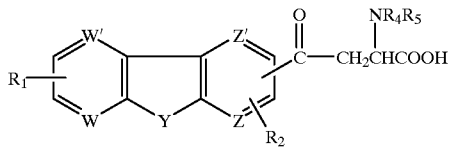

The reactants are combined in approximately equimolar quantities in a solvent such as dichloromethane with an equivalent or excess of aluminum chloride. The acylation typically is complete within about 8 to about 24 hours when carried out at a temperature of about −5° C. to about 20° C. The product is readily isolated by pouring the reaction mixture into ice/water, and separating the organic layer. Removal of the solvent by evaporation affords the invention compound, which can be purified by standard techniques such as chromatography and crystallization.

The compound thus prepared can be converted to other invention compounds (i.e., where one or both of $R_4$ and $R_5$ are other than hydrogen, or where the 4-oxo group is converted to an oxime) by conventional means. For example, a compound of the above formula wherein $R_4$ is hydrogen, and $R_5$ is an acyl group such as trifluoroacetyl readily reacts with ammonia in an alcohol such as methanol to afford the corresponding primary amine, where both $R_4$ and $R_5$ are hydrogen. The primary amine can be acylated or alkylated by conventional means, for example by reaction with an acyl halide such as acetyl chloride or glycyl bromide, a sulfonyl halide such as isopropylsulfonyl chloride or benzylsulfonyl bromide, an anhydride such as acetic anhydride or acetic-formic anhydride, or an alkyl halide such as methyl bromide or ethyl iodide, to provide the corresponding N-acyl or N-alkyl derivative. The butanoic acid esters of the invention, i.e., where $R_3$ is alkoxy or substituted alkoxy, are readily prepared by reacting the free acid of the above formula with an alcohol under acidic conditions, or by other conventional esterification techniques. Such reactions are depicted in Scheme 1.

Scheme 1

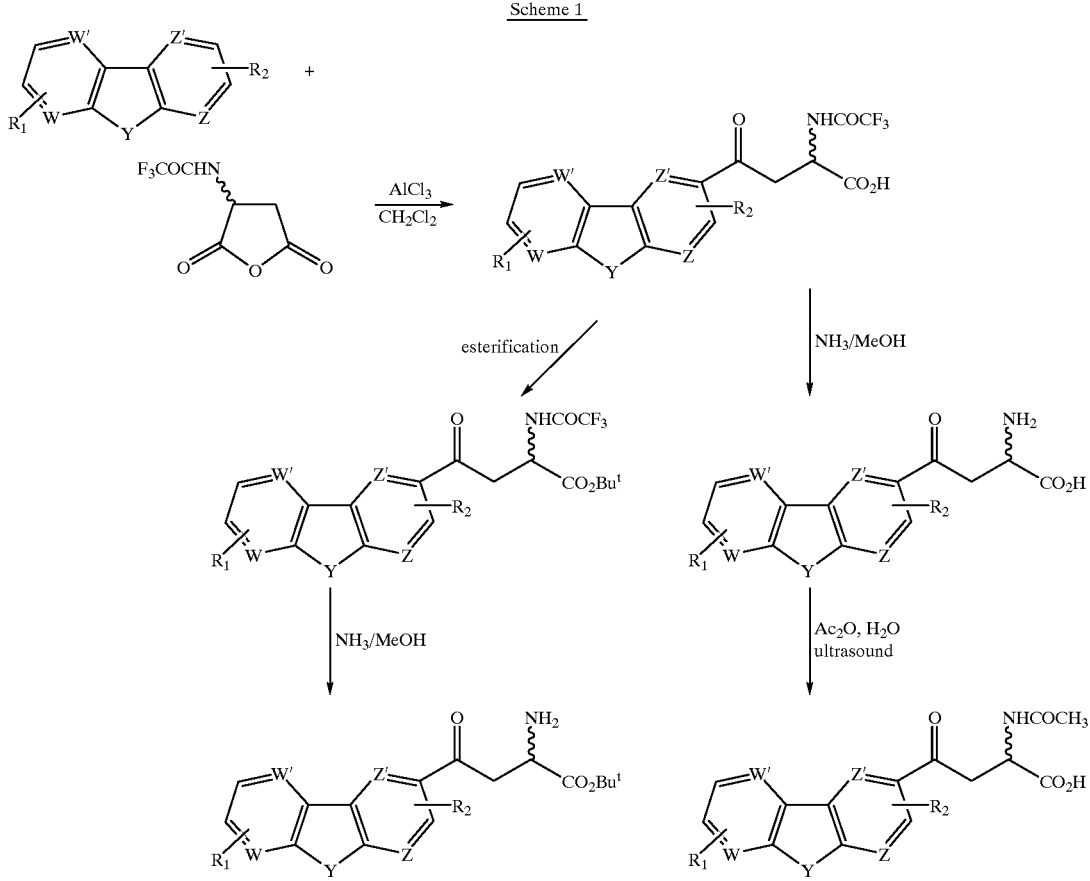

The butyric acid esters of Formula I, compounds wherein $R_3$ is O-alkyl or O-substituted alkyl, are especially useful as intermediates, in that other sites in the molecule can be derivatized, and the ester function can subsequently be hydrolyzed to provide the free acid. The ester groups are readily hydrolyzed to the corresponding carboxylic acids by routine methods, for instance by reaction with a strong acid such as trifluoroacetic acid, polyphosphoric acid, sulfuric acid, or the like. The hydrolysis generally is carried out at a temperature of about 0° C. to about 25° C., and normally is complete within about 2 to 24 hours. The product, a compound of Formula I wherein $R_3$ is OH, can be isolated by diluting the reaction mixture with water and extracting the product into a water immiscible solvent such as ethyl acetate, dichloromethane, or the like, and then removing the organic solvent, for example by evaporation under reduced pressure. The free carboxylic acids thus formed can be converted to salts by reaction with a base such as sodium hydroxide, calcium carbonate, or the like. The carboxylic acids also can be reacted with hydroxylamine hydrochloride to form the corresponding hydroxamic acids, i.e., compounds of Formula I where $R_3$ is NHOH.

The invention compounds contain at least one asymmetric carbon atom, and as such exist as optically active isomers. The invention contemplates the racemic forms as well as the individual isomers. The individual isomers can be prepared from optically pure starting materials, for example by utilizing naturally occurring amino acids, or by resolving the racemate by normal techniques such as chromatography and the like.

Synthesis of various invention compounds of Formula I can be facilitated by utilizing common protecting groups on functional groups such as hydroxy, carboxy, and amino. Protecting groups will be utilized to prevent unwanted side reactions and are readily removed when desired to provide the invention compound. The use of protecting groups is well-documented, for example, by Greene and Wuts in "Protective Groups in Organic Synthesis," 2nd Ed., 1991, John Wiley & Sons, Inc. Typical carboxy acid and hydroxy protecting groups are readily removable ester and ether forming groups such as 2,2,2-trichloroethyl, benzyl, methyl, trimethylsilyl, acetyl, and the like. Primary amino groups, for example, compounds of Formula I wherein $R_4$ and $R_5$ both are hydrogen, are readily protected with common acyl groups such as acetyl, pivaloyl, trifluoroacetyl, trimethylsilyl, and t-butyldimethylsilyl.

A key intermediate for the synthesis of most of the compounds of this invention is the primary amines of Formula I wherein $R_4$ and $R_5$ both are hydrogen. These compounds are prepared as described above and in Scheme 1. In a preferred embodiment, the key intermediate has the formula

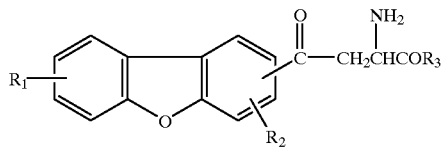

where $R_1$, $R_2$, and $R_3$ are as defined above. Such primary amino compounds readily undergo standard reactions of amines to provide invention compounds of Formula I wherein one or both of $R_4$ and $R_5$ are other than hydrogen. For example, the primary amines react with acylating agents such as acid halides and acid anhydrides to produce the corresponding amides. Typical acid halides that can be utilized include

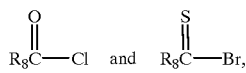

and typical anhydrides include

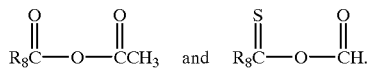

Ureas, e.g., Formula I where $R_4$ is hydrogen and $R_5$ is $CONR_8R_9$, can be prepared by reacting the primary amine with an isocyanate of the formula $R_8-N=C=O$, followed by alkylation or acylation to afford compounds wherein $R_9$ is other than hydrogen. Carbamates and thiocarbamates, e.g., Formula I where $R_4$ is hydrogen and $R_5$ is

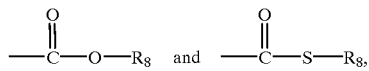

respectively, are prepared by reacting the primary amine with acid halides of the formula

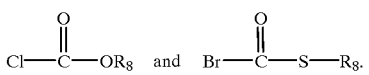

Similar acylations can be carried out with acid halides such as

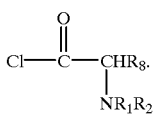

The primary amines (Formula I where $R_4$ and $R_5$ both are H) can also be reacted with chlorocarbonyl isocyanate to give an acid chloride intermediate that can then be reacted with amines, alcohols, and thiols to provide invention compounds. The reaction of the amine and chlorocarbonyl isocyanate is depicted as follows:

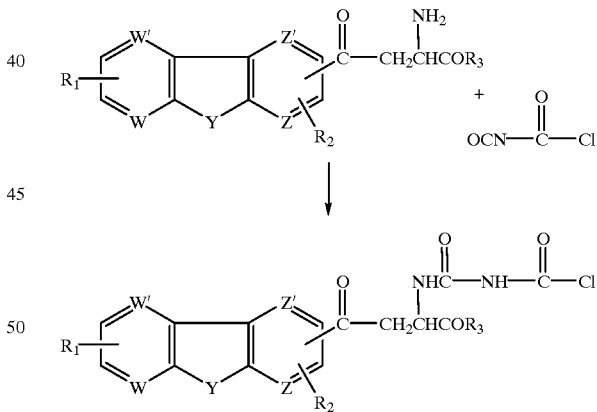

The primary amine and chlorocarbonyl isocyanate generally are mixed in equimolar quantities in an unreactive organic solvent such as diethyl ether or dichloromethane. The reaction generally is complete within about 1 to 2 hours when carried out at about 0° C. The intermediate acid chloride readily reacts with amines, alcohols, and thiols according to the following scheme:

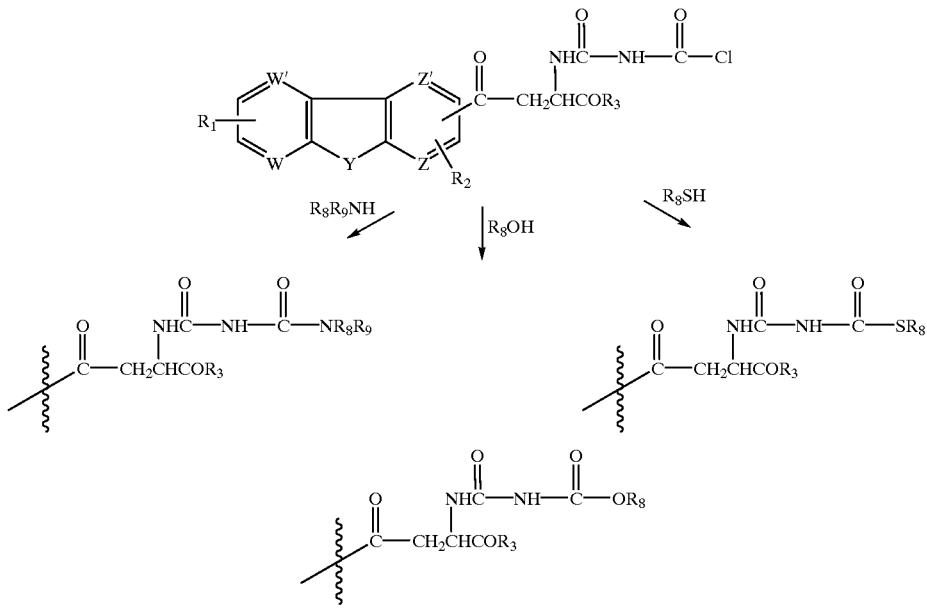
The primary amine (Formula I where $R_4$ and $R_5$ both are hydrogen) can also be reacted with chlorosulfonyl isocyanate to provide a sulfonyl chloride:
-continued
The sulfonyl chloride can be reacted with an amine or alcohol as follows:
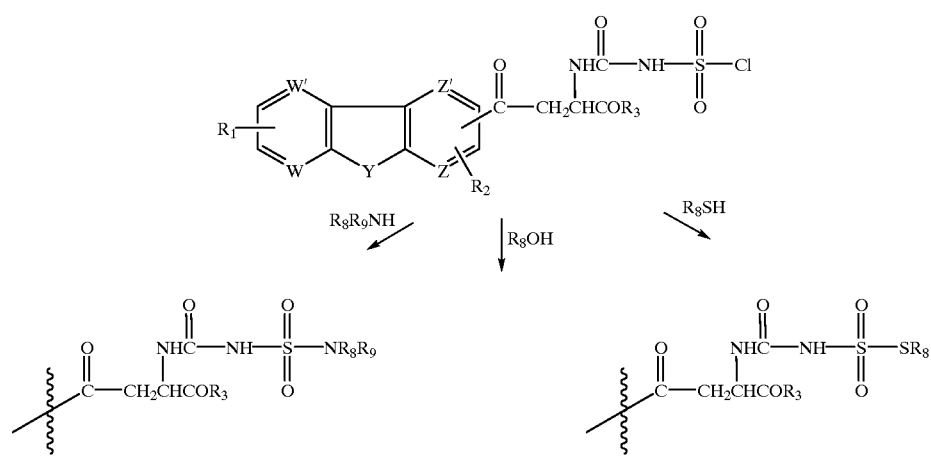

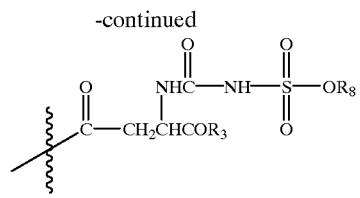

The primary amines can additionally be acylated by reaction with a carboxy acid in the presence of a peptide coupling agent. Typical coupling agents include N,N'-dicyclohexycarbodiimide, N,N'-diisopropylcarbodiimide, N,N'-diethylcarbodiimide, and 1,2-dihydroquinoline.

As noted above, the invention includes pharmaceutically acceptable salts and solvates of compounds having Formula I. The carboxylic acids (i.e., $R_3$ is OH) readily react with inorganic and organic bases to form such salts. Typical inorganic bases commonly employed include sodium hydroxide, potassium carbonate, calcium phosphate, and sodium bicarbonate. Organic bases routinely used include diethylamine, pyridine, benzylamine, triethanolamine, morpholine, and ethylenediamine. Compounds of Formula I which have a basic group, for example when $R_4$ and $R_5$ both are hydrogen, can form acid addition salts by reaction with inorganic or organic acids. Typical acids include hydrochloric acid, sulfuric acid, phosphoric acid, benzoic acid, methanesulfonic acid, p-toluenesulfonic acid and the like. The salts of the invention typically are highly crystalline under normal conditions and can be purified by crystallization from common solvents such as ethyl acetate, chloroform, ethanol, water, toluene, diethyl ether, and hexane. Such crystallizations can produce the invention compound as a solvate, for example as a hydrate or ethanolate, which forms can be utilized in pharmaceutical preparations.

The synthesis of invention compounds is further illustrated in Scheme 2, as well as in the following detailed examples. The examples are illustrative only and are not intended to be limiting in any respect.

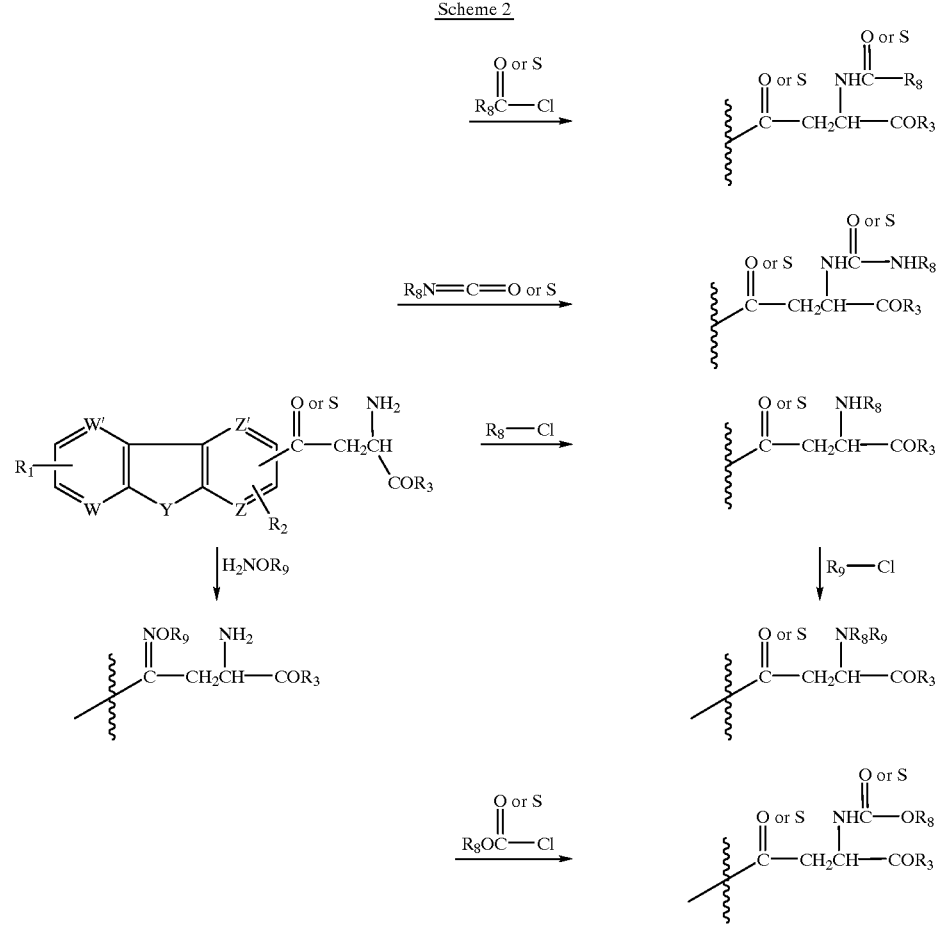

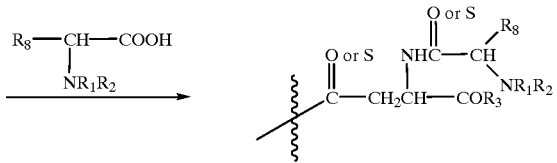

EXAMPLE 1

(S)-4-Dibenzofuran-2-yl-4-oxo-2-(2,2,2-trifluoroacetylamino)-butyric acid

To a dichloromethane (50 mL) suspension of aluminum chloride (3.19 g, 0.024 mol) at 0° C., under an inert nitrogen atmosphere was added via a solid addition funnel an intimate mixture of N-trifluoroacetyl-L-aspartic acid anhydride (3.01 g, 0.0142 mol) and dibenzofuran (2 g, 0.0119 mol). The resulting brick-red suspension was allowed to warm to room temperature over 12 hours. The reaction mixture was poured into ice water (250 mL), and the resulting colorless biphasic mixture was extracted with ethyl acetate (4×100 mL). The combined organic extracts were washed with water (2×100 mL), brine (2×100 mL) and dried over magnesium sulfate. The mixture was filtered, and the organic solution was concentrated by evaporation of the solvent in vacuo to yield a white solid. The solid was recrystallized from 10% ethyl acetate/hexane (v/v) to give (S)-4-dibenzofuran-2-yl-4-oxo-2-(2,2,2-trifluoroacetylamino)-butyric acid (2.16 g, 48%) as a while solid; mp 174–176° C.

EXAMPLE 2

(R)-4-Dibenzofuran-2-yl-4-oxo-2-(2,2,2-trifluoroacetylamino)-butyric acid

The general procedure of Example 1 was repeated, utilizing N-(trifluoroacetyl)-D-aspartic acid anhydride to provide (R)-4-dibenzofuran-2-yl-4-oxo-2-(2,2,2-trifluoroacetylamino)-butyric acid; mp 140–144° C.

EXAMPLE 3

(S)-2-Amino-4-dibenzofuran-2-yl-4-oxo-butyric acid

Methanol (40 mL) was saturated with gaseous ammonia at room temperature. To this solution was added (S)-4-dibenzofuran-2-yl-4-oxo-2-(2,2,2-trifluoroacetylamino)-butyric acid (0.5 g, 0.0013 mol) obtained above in Example 1. The reaction mixture was stirred at room temperature for 24 hours and then concentrated to dryness in vacuo. The residue was recrystallized from boiling methanol to yield the title product as a white solid (0.37 g, quant); mp 182–187° C.

EXAMPLE 4

(S)-2-Acetylamino-4-dibenzofuran-2-yl-4-oxo-butyric acid

A suspension of (S)-2-amino-4-dibenzofuran-2-yl-4-oxo-butyric acid (0.025 g, 0.000082 mol) obtained above in Example 3 in acetic anhydride (2 mL) and water (4 mL) was sonicated (Cole Parmer 8850 Ultrasound Bath) for 15 minutes at room temperature. The resulting solution was then concentrated in vacuo, and the resulting residue was recrystallized from ethyl acetate/diethyl ether (50:50, v/v) to yield the title product as a white solid; mp 166–170° C.

EXAMPLE 5

(S)-4-Dibenzofuran-2-yl-2-[3-(2,6-diisopropyl-phenyl)-ureido]-4-oxo-butyric acid Step (a) (S)-4-Dibenzofuran-2-yl-4-oxo-2-(2,2,2-trifluoroacetylamino)-butyric acid tert-butyl ester To a DMF solution (10 mL) of (S)-4-dibenzofuran-2-yl-4-oxo-2-(2,2,2-trifluoroacetylamino)-butyric acid (0.3 g, 0.00079 mol) at 40° C. was added carbonyldimidazole (0.13 g, 0.00079 mol). This mixture was stirred for 1 hour and then 1,8-diazabicyclo-[5.4.0]undec-7-ene (DBU, 0.12 mL, 0.00079 mol) and t-butanol (0.15 mL, 0.00158 mol) were added. The reaction mixture was stirred for 24 hours at 40° C., cooled to 24° C., and then diluted with ether (20 mL). The solution was washed with water (2×10 mL), brine (2×10 mL), and dried over anhydrous magnesium sulfate. The mixture was filtered and the filtrate was concentrated to an oil by evaporation of the solvent in vacuo. The oil was flash chromatographed on silica gel eluting with 20% ethyl acetate/hexane (v/v) to yield the title compound; mp 92–94° C.

Step (b) (S)-4-Dibenzofuran-2-yl-2-[3-(2,6-diisopropoyl-phenyl)-ureido]-4-oxo-butyric acid tert-butyl ester Into a methanolic solution (100 mL) of the compound from Step (a) above (0.22 g, 0.000505 mol) was bubbled ammonia gas at room temperature for 5 minutes. The reaction mixture was stirred at room temperature for 18 hours. The solution was then concentrated and flash chromatographed on silica gel eluting with ethyl acetate to give (S)-2-amino-4-dibenzofuran-2-yl-4-oxo-butyric acid, t-butyl ester (0.112 g, 65%) which was used in the next step without further purification.

To a stirred ethyl acetate solution (5 mL) of the product from Step (b) (0.112 g, 0.00033 mol) was added 2,6-diisopropylphenylisocyanate (0.067 g, 0.00033 mol) at room temperature under an inert nitrogen atmosphere. The reaction mixture was stirred for 48 hours after which time the solution was concentrated in vacuo and flash chromatographed on silica gel eluting with 50% ethyl acetate/hexane (v/v) to yield (S)-4-dibenzofuran-2-yl-2-[2,6-diisopropylphenyl)-ureido]-4-oxo-butyric acid tert-butyl ester (0.05 g, 28%); mp 94–97° C.

Step (c) (S)-4-Dibenzofuran-2-yl-2-[3-(2,6-diisopropyl-phenyl)-ureido]-4-oxo-butyric acid To a dichloromethane solution (2 mL) of the product obtained above in Step (b) (0.05 g, 0.000092 mol) was added trifluoroacetic acid (1 mL) and one drop of anisole at room temperature with stirring. After 7 hours, the solution was concentrated and the residue triturated with diethyl ether. The solid obtained was filtered and air dried to yield (S)-4-dibenzofuran-2-yl-2-[3-(2,6-diisopropyl-phenyl)-ureido]-4-oxo-butyric acid (0.025 g, 56%); mp 205–210° C. (dec).

EXAMPLE 6

(S)-2-Benzoylamino-4-dibenzofuran-2-yl-4-oxo-butyric acid

Step (a) (S)-2-Amino-4-dibenzofuran-2-yl-4-oxo-butyric acid, methyl ester, hydrochloride Into a methanolic solution (250 mL) of (S)-4-dibenzofuran-2-yl-4-oxo-2-(2,2,2-trifluoroacetylamino)-butyric acid (1.75 g, 0.0046 mol) was bubbled gaseous hydrogen chloride for 3 hours at room temperature. The solution was then concentrated in vacuo, and the resulting solid was triturated with a mixture of ethyl acetate and diethyl ether (1:1, v/v) to yield the title compound (1.22 g, 77%);

mp 156–160° C.

Step (b) (S)-2-Benzoylamino-4-dibenzofuran-2-yl-4-oxo-butyric acid methyl ester

To a THF/water (1:1, 10 mL) solution of the material obtained above in Step (a) (0.5 g, 0.0015 mol) was added triethylamine (0.22 mL, 0.0015 mol). The resulting suspension was stirred at room temperature for 30 minutes, at which time more triethylamine (0.22 mL, 0.0015 mol) and benzoyl chloride (0.21 g, 0.0015 mol) were added. The reaction mixture was stirred at room temperature for 1 hour and then diluted with 50 mL of water. The solution was extracted with ethyl acetate (2×50 mL). The organic extract was washed with water (2×50 mL) and brine (2×50 mL) and dried over anhydrous magnesium sulfate. The solution was filtered and the filtrate was concentrated in vacuo. Flash chromatography on silica gel eluting with 50% ethyl acetate/hexane (v/v) gave (S)-2-benzoylamino-4-dibenzofuran-2-yl-4-oxo-butyric acid methyl ester (0.39 g, 65%); mp 65–70° C.

Step (c) (S)-2-Benzoylamino-4-dibenzofuran-2-yl-4-oxo-butyric acid

To a dioxan/water solution (1:1, 30 mL) of the material obtained above in Step (b) (0.32 g, 0.000797 mol) was added lithium hydroxide monohydrate (0.07 g, 0.00168 mol). The resulting suspension was stirred at room temperature for 4 hours. The reaction mixture was concentrated in vacuo and the residue re-dissolved in water (10 mL) and cooled in an ice bath. The cold solution was acidified to pH 2.0 with aqueous 1N HCl. The precipitate which formed was collected by filtration and air dried to yield (S)-2-Benzoylamino-4-dibenzofuran-2-yl-4-oxo-butyric acid (0.29 g, 94%); mp 124–130° C.

Following the general procedure of Example 6, the following compounds were obtained:

EXAMPLE 7
(S)-4-Dibenzofuran-2-yl-4-oxo-2-phenylacetylamino-butyric acid;

mp 94–98° C.

EXAMPLE 8
(S)-4-Dibenzofuran-2-yl-4-oxo-2-(3-phenylpropionylamino)-butyric acid;

mp 118–121° C.

EXAMPLE 9
(S)-4-Dibenzofuran-2-yl-4-oxo-2-(7-phenylheptanoylamino)-butyric acid;

mp 105–108° C.

EXAMPLE 10
(S)-2-[(Biphenyl-4-carbonyl)-amino]-4-dibenzofuran-2-yl-4-oxo-butyric acid $^1$H NMR (DMSO-D$_6$): δ 8.9 (s, 1H), 8.8 (m, 1H), 8.3–7.4 (m, 16H), 5.1 (m, 1H), 3.8 (m, 2H) ppm.

EXAMPLE 11
(S)-4-Dibenzofuran-2-yl-4-oxo-2-(octanoylamino)-butyric acid;

mp 57–60° C.

EXAMPLE 12
(S)-4-Dibenzofuran-2-yl-4-oxo-2-(dodecanoylamino)-butyric acid;

mp 85–88° C.

EXAMPLES 13–14

Following the general procedure of Example 6, except substituting a sulfonyl chloride for the benzoyl chloride utilized in Step (b), the following sulfonamides were prepared:

(S)-4-Dibenzofuran-2-yl-4-oxo-2-methanesulfonylamino-butyric acid; mp 161–168° C.;

(S)-4-Dibenzofuran-2-yl-4-oxo-2-(4-methylphenylsulfonylamino)-butyric acid;

$^1$H NMR (DMSO-d$_6$): δ 8.9 (s, 1H), 7.2–8.3 (m, 11H), 4.5 (m, 1H), 3.6 (m, 2H), 2.8 (m, 1H), 2.2 (s, 3H) ppm.

EXAMPLE 15

By following the procedure of Example 1, except using fluorene instead of dibenzofuran, there was obtained the compound (S)-4-(9H-fluoren-2-yl)-4-oxo-2-(2,2,2-trifluoroacetylamino)-butyric acid;

mp 111–115° C.

EXAMPLE 16
(S)-4-Dibenzofuran-2-yl-4-hydroxyimino-2-(2,2,2-trifluoroacetylamino)-butyric acid To a solution of (S)-4-dibenzofuran-2-yl-4-oxo-2,2,2-trifluoroacetylamino)-butyric acid (1.0 g, 0.0026 mol) from Example 1 in 50 mL of methanol was added sodium acetate trihydrate (1.08 g, 0.0079 mol). The solution was stirred at 24° C. while an aqueous solution (5 mL) of hydroxylamine hydrochloride (0.37 g, 0.00527 mol) was added in one portion. The reaction mixture was stirred for 3 hours at 24° C., and then heated to reflux for 2 hours. The solution was cooled to 24° C. and concentrated to dryness by evaporation under reduced pressure. The solid was rinsed with 10 mL of water, and crystallized from ethyl acetate and hexane to afford 0.13 g of (S)-4-dibenzofuran-2-yl-4-hydroxyimino-2-(2,2,2-trifluoroacetylamino)-butyric acid; mp 128–130° C.

EXAMPLE 17

(S)-2-Benzoylamino-4-dibenzofuran-2-yl-4-oxo-butyric acid methyl ester, prepared as described in Step (b) of Example 6, was dissolved in tetrahydrofuran containing one equivalent of triethylamine. The solution was stirred at room temperature for 1 hour, and then the solvent was removed by evaporation to give a solid. The solid was washed with water to give methyl (S)-2-amino-4-dibenzofuran-2-yl-4-oxo-butyrate as a mono-hydrate.

EXAMPLES 18–55

Several invention compounds of Formula I were prepared by combinatorial synthetic techniques. The general procedure utilized is as follows:

A 0.17 molar stock solution was made by dissolving 2.9 g (8.69 mmol) of 2-amino-4-dibenzofuran-2-yl-4-oxo-butyric acid methyl ester hydrochloride (prepared as in Step (a) of Example 6) in 50 mL of dichloromethane. One milliliter of this solution was added to 38 separate vials, along with 70 mg of a morpholino-resin (prepared according to Booth R. J. and Hodges J. C., *J. Am. Chem. Soc.*, 1997;119(21):4882–4886). 1.1 Equivalents (0.187 mmol) of the appropriate carboxylic acid chloride was added to each of the 38 vials. The vials were sealed and shaken for 54 hours at room temperature. An excess of an amino-resin and an isocyanato-resin (both prepared according to Booth and Hodges, Supra., 1997) was added to each vial, and the vials were shaken for 16 hours to quench unreacted starting materials. Each reaction mixture was filtered through a plug of glass wool, and the resins were washed with 2 mL tetrahydrofuran. The filtrate was evaporated under a stream of nitrogen, and the residue in each vial was re-dissolved in 1 mL tetrahydrofuran. One milliliter of a 0.315 molar aqueous solution of lithium hydroxide was added to each vial, and the resulting mixtures were again shaken for 16 hours. Each reaction mixture was washed with diethyl ether, and the aqueous layer was then acidified with 1 molar hydrochloric acid. The products were extracted into ethyl acetate, and the solvent was evaporated under a stream of nitrogen for 54 hours to leave the desired products. The compounds were analyzed by LC/MS to determine purity and presence of expected ion.

The foregoing reaction is depicted in the following generalized scheme:

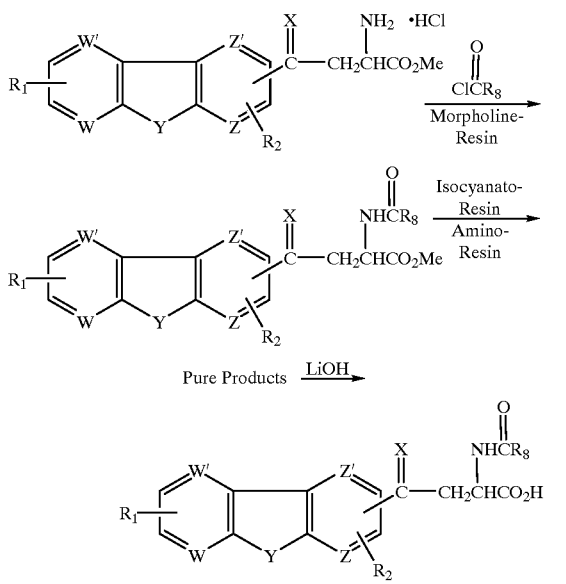

The following specific invention compounds were prepared by the foregoing combinatorial methodology:

| Example No. | Compound | MS (m + 1) |
|---|---|---|
| 18 | 4-Dibenzofuran-2-yl-2-diphenylacetylamino-4-oxo-butyric acid | 478 |
| 19 | 2-[2-(4-Chloro-phenoxy)-acetylamino]-4-dibenzofuran-2-yl-4-oxo-butyric acid | 452 |
| 20 | 4-Dibenzofuran-2-yl-2-(3,4-dichloro-benzoylamino-4-oxo-butyric acid | 456 |
| 21 | 4-Dibenzofuran-2-yl-2-[2-(3,4-dimethoxy-phenyl)-acetylamino]-4-oxo-butyric acid | 462 |
| 22 | 4-Dibenzofuran-2-yl-2-[(naphthalene-2-carbonyl)-amino]-4-oxo-butyric acid | — |
| 23 | 4-Dibenzofuran-2-yl-2-(2,2-dimethyl-pentanoylamino)-4-oxo-butyric acid | 396 |
| 24 | 4-Dibenzofuran-2-yl-4-oxo-2-[(pyridine-4-carbonyl)-amino]-butyric acid | — |
| 25 | 4-Dibenzofuran-2-yl-4-oxo-2-(3-phenyl-acryloylamino)-butyric acid | 414 |
| 26 | 2-[(Adamantane-1-carbonyl)-amino]-4-dibenzofuran-2-yl-4-oxo-butyric acid | — |
| 27 | 4-Dibenzofuran-2-yl-4-oxo-2-(2,2,3,3,4,4,5,5,6,6,7,7,8,8,8-pentadecafluoro-octanoylamino)-butyric acid | — |
| 28 | 4-Dibenzofuran-2-yl-4-oxo-2-(2-phenoxy-acetylamino)-butyric acid | 418 |
| 29 | 4-Dibenzofuran-2-yl-2-(4-methyl-benzoylamino)-4-oxo-butyric acid | 402 |
| 30 | 4-Dibenzofuran-2-yl-4-oxo-2-(2-phenoxy-propionylamino)-butyric acid | 432 |
| 31 | 2-[4-(4-Bromo-phenyl)-butyrylamino]-4-dibenzofuran-2-yl-4-oxo-butyric acid | 508 |
| 32 | 2-(2-Benzyloxy-acetylamino)-4-dibenzofuran-2-yl-4-oxo-butyric acid | 432 |
| 33 | 4-Dibenzofuran-2-yl-2-heptanoylamino-4-oxo-butyric acid | 396 |
| 34 | 2-(4-Butyl-benzoylamino)-4-dibenzofuran-2-yl-4-oxo-butyric acid | 444 |
| 35 | 2-(4-Cyano-benzoylamino)-4-dibenzofuran-2-yl-4-oxo-butyric acid | 413 |
| 36 | 2-[(3-Chloro-thiophene-2-carbonyl)-amino)-4-dibenzofuran-2-yl-4-oxo-butyric acid | 428 |
| 37 | 2-(4-Butoxy-benzoylamino)-4-dibenzofuran-2-yl-4-oxo-butyric acid | 460 |
| 38 | 2-(Cyclopropanecarbonyl-amino)-4-dibenzofuran-2-yl-4-oxo-butyric acid | 352 |
| 39 | 2-(4-Chloro-benzoylamino)-4-dibenzofuran-2 -yl-4-oxo-butyric acid | 422 |
| 40 | 4-Dibenzofuran-2-yl-4-oxo-2-(2,3,4,5,6-pentafluoro-benzoylamino)-butyric acid | — |
| 41 | 4-Dibenzofuran-2-yl-2-[(furan-2-carbonyl)-amino]-4-oxo-butyric acid | 378 |
| 42 | 2-(4-Bromo-benzoylamino)-4-dibenzofuran-2-yl-4-oxo-butyric acid | 466 |
| 43 | 4-Dibenzofuran-2-yl-2-(4-fluoro-benzoylamino)-4-oxo-butyric acid | 406 |
| 44 | 4-Dibenzofuran-2-yl-4-oxo-2-[(quinoxaline-2-carbonyl)-amino]-butyric acid | 440 |
| 45 | 4-Dibenzofuran-2-yl-4-oxo-2-[(pyridine-2-carbonyl)-amino]-butyric acid | 389 |
| 46 | 4-Dibenzofuran-2-yl-2-(4-methoxy-benzoylamino)-4-oxo-butyric acid | 418 |
| 47 | 4-Dibenzofuran-2-yl-2-(3,4-dimethoxy-benzoylamino)-4-oxo-butyric acid | 448 |
| 48 | 4-Dibenzofuran-2-yl-4-oxo-2-(4-trifluoromethyl-benzoylamino)-butyric acid | 456 |
| 49 | 2-(Cyclopentanecarbonyl-amino)-4-dibenzofuran-2-yl-4-oxo-butyric acid | 380 |
| 50 | 2-(Cyclohexanecarbonyl-amino)-4-dibenzofuran-2-yl-4-oxo-butyric acid | 394 |
| 51 | 4-Dibenzofuran-2-yl-4-oxo-2-[(thiophene-2-carbonyl)-amino]-butyric acid | 394 |
| 52 | 4-Dibenzofuran-2-yl-4-oxo-2-(2-thiophen-2-yl-acetylamino)-butyric acid | — |
| 53 | 2-[(Benzo[1,3]dioxole-5-carbonyl)-amino]-4-dibenzofuran-2-yl-4-oxo-butyric acid | 432 |
| 54 | 4-Dibenzofuran-2-yl-4-oxo-2-(2-phenylbutyrylamino)-butyric acid | 430 |
| 55 | 4-Dibenzofuran-2-yl-2-[(5-methyl-2-phenyl-2H-[1,2,3]triazole-4- | 469 |

| Example No. | Compound | MS (m + 1) |
|---|---|---|
| | carbonyl)-amino]-4-oxo-butyric acid | |

The invention compounds have been evaluated in standard in vitro assays and shown to be potent inhibitors of several matrix metalloproteinase enzymes. The assays measure the amount by which a test compound reduces the hydrolysis of a thiopeptolide substrate caused by a matrix metalloproteinase enzyme. Such assays are described in detail by Ye, et al., in Biochemistry, 1992;31(45):11231–11235).

Thiopeptolide substrates show virtually no decomposition or hydrolysis in the absence of a matrix metalloproteinase enzyme. A typical thiopeptolide substrate commonly utilized for assays is Ac-Pro-Leu-Gly-thioester-Len-Len-Gly-O Et. A 100 µL assay mixture will contain 50 mM of 2-morpholinoethane sulfonic acid monohydrate (MES, pH 6.0) 10 mM $CaCl_2$, 100 µM thiopeptolide substrate, and 1 mM 5,5'-dithio-bis-(2-nitro-benzoic acid (DTNB). The thiopeptolide substrate concentration is varied from 10 to 800 µM to obtain Km and Kcat values. The change in absorbance at 405 nm is monitored on a Thermo Max microplate reader (molecular Devices, Menlo Park, Calif.) at room temperature (22° C.). The calculation of the amount of hydrolysis of the thiopeptolide substrate is based on $E_{412}=13600$ $m^{-1}$ $cm^{-1}$ for the DTNB-derived product 3-carboxy-4-nitrothiophenoxide. Assays are carried out with and without matrix metalloproteinase inhibitor compounds, and the amount of hydrolysis is compared for a determination of inhibitory activity of the test compounds.

Several representative compounds have been evaluated for their ability to inhibit various matrix metalloproteinase enzymes. Table I below presents inhibitory activity for several invention compounds. In the table, MMP-1 refers to interstitial collagenase; MMP-2 refers to Gelatinase A; MMP-3 refers to stromelysin; MMP-7 refers to matrilysin; and MMP-13 refers to Collagenase 3. Test compounds were evaluated at various concentrations in order to determine their respective $IC_{50}$ values, the micromolar concentration of compound required to cause a 50% inhibition of the hydrolytic activity of the respective enzyme.

TABLE I

| Compound of Example No. | ($IC_{50}$) µM | | | | |
|---|---|---|---|---|---|
| | MMP-1 | MMP-2 | MMP-3 | MMP-7 | MMP-13 |
| 1 | 100 | 0.059 | 0.95 | 100 | 2.8 |
| 2 | — | 44.0 | 78 | — | — |
| 3 | — | 3.8 | 33 | — | — |
| 4 | — | 0.16 | 1.6 | — | — |
| 5 | — | 0.32 | 1.7 | — | — |
| 6 | — | 0.18 | 0.91 | — | — |
| 7 | — | 0.084 | 0.33 | — | — |
| 8 | 100 | 0.067 | 0.29 | 100 | 1.3 |
| 9 | — | 0.51 | 3.9 | — | — |
| 10 | — | 1.64 | 9.4 | — | — |
| 11 | 100 | 0.36 | 2.7 | 100 | 6.8 |
| 12 | 100 | 8.8 | 4.0 | — | — |
| 13 | — | 0.28 | 9.2 | 100 | — |
| 14 | 83 | 0.017 | 0.26 | 100 | 1.1 |
| 15 | 100 | 12.5 | 76.5 | 100 | 100 |
| 16 | 100 | 0.72 | 6.6 | 100 | 2.4 |
| 18 | 100 | 0.1 | 0.36 | 100 | 1.1 |
| 19 | 100 | 0.64 | 3.1 | 100 | 46 |
| 20 | 100 | 1.3 | 7.0 | 100 | 38 |
| 21 | 100 | 0.32 | 2.4 | 100 | 16 |
| 22 | 100 | 1.7 | 6.9 | 100 | 28 |
| 23 | 100 | 0.17 | 0.76 | 100 | 5.6 |
| 24 | 100 | 3.2 | 13.0 | 100 | 41 |
| 25 | 100 | 0.11 | 0.8 | 100 | 8.4 |
| 26 | 100 | 2.1 | 9.2 | 100 | 40 |
| 27 | 100 | 4.6 | 18 | 100 | 77 |
| 28 | 100 | 0.18 | 0.51 | 100 | 12 |
| 29 | 100 | 0.05 | 0.39 | 100 | 5.2 |
| 30 | 45 | 0.035 | 0.1 | 100 | 2.9 |
| 31 | 100 | 0.6 | 5.3 | 100 | 25 |
| 32 | 100 | 0.041 | 0.33 | 100 | 3.5 |
| 33 | 100 | 0.06 | 0.64 | 100 | 4.7 |
| 34 | 100 | 0.87 | 5.4 | 100 | 49 |
| 35 | 100 | 0.11 | 1.1 | 100 | 11 |
| 36 | 100 | 0.14 | 1.0 | 100 | 13 |
| 37 | 100 | 0.8 | 5.0 | 100 | 58 |
| 38 | 100 | 0.09 | 0.85 | 100 | 5.6 |
| 39 | 100 | 0.15 | 1.2 | 100 | 12 |
| 40 | 100 | 5.2 | 28 | 100 | 100 |
| 41 | 100 | 0.14 | 1.5 | 100 | 12 |
| 42 | 100 | 0.18 | 1.3 | 100 | 17 |
| 43 | 100 | 0.07 | 0.66 | 100 | 7.1 |
| 44 | 100 | 0.31 | 3.5 | 100 | 27 |
| 45 | 100 | 0.11 | 1.0 | 100 | 15 |
| 46 | 100 | 0.14 | 1.0 | 100 | 11 |
| 47 | 100 | 0.13 | 0.87 | 100 | 8.8 |
| 48 | 100 | 0.32 | 1.5 | 100 | 20 |
| 49 | 100 | 0.08 | 0.35 | 100 | 4.4 |
| 50 | 100 | 0.15 | 0.7 | 100 | 9.1 |
| 51 | 100 | 0.16 | 1.3 | 100 | 16 |
| 52 | 100 | 2.5 | 7.7 | 100 | 48 |
| 53 | 100 | 0.13 | 1.0 | 100 | 9.2 |
| 54 | 100 | 0.06 | 0.25 | 100 | 1.5 |
| 55 | 100 | 1.8 | 14 | 100 | 70 |

The compounds were additionally evaluated for their ability to inhibit full-length collagenase hydrolysis of thiopeptolide substrate (FLC) and full-length gelatinase B (FLGB) hydrolysis of thiopeptolide. The results of representative compounds is given in Table II.

TABLE II

| Compound of Example No. | ($IC_{50}$) µM | |
|---|---|---|
| | FLC | FLGB |
| 1 | >100 | >100 |

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I. The active compound generally is present in a concentration of about 5% to about 95% by weight of the formulation.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg according to the particular application and the potency of the active component. The composition can, if desired, also contain other compatible therapeutic agents.

In therapeutic use as agents for the treatment of multiple sclerosis, atherosclerotic plaque rupture, aortic aneurism, heart failure, restenosis, periodontal disease, corneal ulceration, cancer metastasis, tumor angiogenesis, arthritis, or other autoimmune or inflammatory disorders dependent upon breakdown of connective tissue, the compounds utilized in the pharmaceutical method of this invention are administered at a dose that is effective to inhibit the hydrolytic activity of one or more matrix metalloproteinase enzymes. The initial dosage of about 1 mg to about 100 mg per kilogram daily will be effective. A daily dose range of about 25 mg to about 75 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired. Typical dosages will be from about 0.1 to about 500 mg/kg, and ideally about 25 to about 250 mg/kg.

The following examples illustrate typical formulations provided by the invention.

EXAMPLE 56

| Tablet Formulation | |
|---|---|
| Ingredient | Amount (mg) |
| 2-N-methylbutyrylamino-4-(6-chlorodibenzofuran-2-yl)-4-thioxo-butyric acid | 25 |
| Lactose | 50 |
| Corn starch (for mix) | 10 |
| Corn starch (paste) | 10 |
| Magnesium stearate (1%) | 5 |
| Total | 100 |

The dibenzofuranyl butanoic acid, lactose, and corn starch (for mix) are blended to uniformity. The corn starch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four times a day for treatment of atherosclerosis, arthritis, and heart failure, including ventricular dilatation.

EXAMPLE 57

| Preparation for Oral Solution | |
|---|---|
| Ingredient | Amount |
| 2-Amino-4-carbazol-2-yl-4-hydroxyimino butyric acid sodium salt | 400 mg |
| Sorbitol solution (70% N.F.) | 40 mL |
| Sodium benzoate | 20 mg |
| Saccharin | 5 mg |
| Red dye | 10 mg |
| Cherry flavor | 20 mg |
| Distilled water q.s. | 100 mL |

The sorbitol solution is added to 40 mL of distilled water, and the carbazolyl butyric acid is dissolved therein. The saccharin, sodium benzoate, flavor, and dye are added and dissolved. The volume is adjusted to 100 mL with distilled water. Each milliliter of syrup contains 4 mg of invention compound.

EXAMPLE 58
Parenteral Solution

In a solution of 700 mL of propylene glycol and 200 mL of water for injection is suspended 20 g of (S)-2-N,N-diethylamino-4-fluoren-3-yl-4-thioxo-butyric acid. After suspension is complete, the pH is adjusted to 6.5 with 1 N sodium hydroxide, and the volume is made up to 1000 mL with water for injection. The formulation is sterilized, filled into 5.0 mL ampoules each containing 2.0 mL, and sealed under nitrogen.

As matrix metalloproteinase inhibitors, the compounds of Formula I are useful as agents for the treatment of multiple sclerosis. They are also useful as agents for the treatment of atherosclerotic plaque rupture, restenosis, periodontal disease, corneal ulceration, treatment of burns, decubital ulcers, wound repair, cancer metastasis, tumor angiogenesis, arthritis, and other inflammatory disorders dependent upon tissue invasion by leukocytes.

We claim:
1. A compound of the Formula I

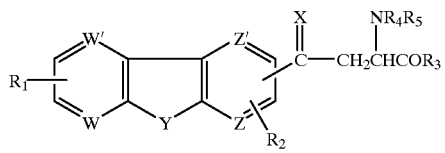

wherein:
X is O, $NOR_9$, S, OH, SH, or

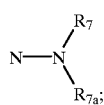

$R_7$ and $R_{7a}$, independently are
hydrogen,
$C_1-C_{20}$ alkyl or substituted $C_1-C_{20}$ alkyl,
$(CH_2)_{0-6}$-aryl,
dibenzofuran, furan or
$(CH_2)_{0-6}$-cycloalkyl;
$R_1$ and $R_2$ independently are
hydrogen,
$C_1-C_{20}$ alkyl or substituted $C_1-C_{20}$ alkyl,
halo,
$NO_2$,
CN,
CHO,
$COR_6$,
$COOR_6$,
$SO_3R_6$,
$OR_6$,
$CONR_4R_5$,
$(CH_2)_{0-6}$-aryl,
dibenzofuran, furan or
$(CH_2)_{0-6}$-cycloalkyl;
R is hydrogen,
$C_1-C_{20}$ alkyl or substituted $C_1-C_{20}$ alkyl;
aryl is phenyl or substituted phenyl;
$R_3$ is hydroxy,
$O-C_1-C_{20}$ alkyl or substituted $O-C_1-C_{20}$ alkyl,
$O-(CH_2)_{1-3}$ aryl, or
$NHOR_6$;
$R_4$ and $R_5$ independently are hydrogen,
$C_1-C_{20}$ alkyl or substituted $C_1-C_{20}$ alkyl,
$C_2-C_{20}$ alkenyl or substituted $C_2-C_{20}$ alkenyl,
$(CH_2)_{0-6}$-aryl,
$(CH_2)_{0-6}$-(O or S)-aryl,
dibenzofuran, furan;
or one of $R_4$ and $R_5$ is hydrogen and the other is:
$COR_8$,
$CSR_8$,
$CONR_8R_9$,
$CSNR_8R_9$,
$COOR_8$,
$COSR_8$, $\underset{NR_1R_2,}{COCHR_8,}$ $\underset{R_1}{CON{-\!\!\!-}CONR_8R_9,}$ $\underset{R_1}{CON{-\!\!\!-}COOR_8,}$ $\underset{R_1}{CON{-\!\!\!-}COSR_8;}$ $\underset{R_1}{CON{-\!\!\!-}SO_2NR_8R_9;}$ $\underset{R_1}{CON{-\!\!\!-}SO_3R_8;}$ $S(O)_{1\ or\ 2}$-$C_1-C_{20}$ alkyl or substituted alkyl,
$S(O)_{1\ or\ 2}$-aryl,
dibenzofuran, furan or
$S(O)_{1\ or\ 2}$-cycloalkyl;
Y is
—O—,
$R_8$ and $R_9$ independently are
hydrogen,
$C_1-C_{20}$ alkyl or substituted $C_1-C_{20}$ alkyl,
$C_2-C_{20}$ alkenyl or substituted $C_2-C_{20}$ alkenyl,
$(CH_2)_{0-6}$-(O or S)$_{0-1}$-aryl,
dibenzofuran, furan or
$(CH_2)_{0-6}$-(O or S)$_{0-1}$-cycloalkyl;

W, W¹, Z, and Z¹ independently are $CR_1$;

or a pharmaceutically acceptable salt, isomer, stereoisomer, or and solvate thereof.

2. A compound of claim 1 having the formula

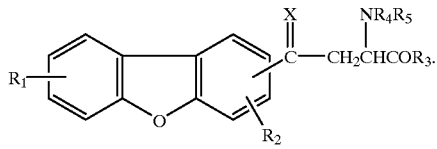

3. A compound of claim 2 having the formula

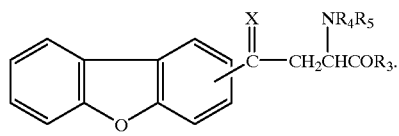

4. A compound of claim 3 wherein X is O.
5. A compound of claim 4 wherein $R_3$ is $C_1$–$C_{20}$ alkoxy.
6. A compound of claim 4 wherein $R_3$ is OH.
7. A compound of claim 6 wherein $R_4$ is H.
8. A compound of claim 7 wherein $R_5$ is H.
9. The compound of claim 8 which is (S)-2-amino-4-dibenzofuran-2-yl-4-oxo-butyric acid.
10. A compound of claim 7 wherein $R_5$ is —$COCH_3$.
11. The compound of claim 10 which is S-2-acetylamino-4-dibenzofuran-2-yl-4-oxo-butyric acid.
12. A compound of claim 7 wherein $R_5$ is —$COCF_3$.
13. The compound of claim 12 which is (S)-2-(2,2,2-trifluoroacetylamino)-4-dibenzofuran-2-yl-4-oxo- butyric acid.
14. The compound of claim 12 which is (R)-2-(2,2,2-trifluoroacetylamino)-4-dibenzofuran-2-yl-4-oxo- butyric acid.
15. A compound of claim 7 wherein $R_5$ is

and $R_8$ is $(CH_2)_{0-6}$-(O or S)$_{0-1}$-aryl or dibenzofuran or furan.

16. A compound of claim 15 selected from the group consisting of (S)-2-Benzoylamino-4-dibenzofuran-2-yl-4-oxo-butyric acid;

(S)-4-Dibenzofuran-2-yl-4-oxo-2-phenylacetylamino-butyric acid;

(S)-4-Dibenzofuran-2-yl-4-oxo-2-(3-phenyl-propionylamino)-butyric acid;

(S)-4-Dibenzofuran-2-yl-4-oxo-2-(7-phenyl-heptanoylamino)-butyric acid;

(S)-2-[(Biphenyl-4-carbonyl)-amino]-4-dibenzofuran-2-yl-4-oxo-butyric acid;

2-[2-(4–Chloro-phenoxy)-acetylamino]-4-dibenzofuran-2-yl-4-oxo-butyric acid;

4-Dibenzofuran-2-yl-2-(3,4-dichloro-benzoylamino4-oxo-butyric acid;

4-Dibenzofuran-2-yl-2-[2-(3,4-dimethoxy-phenyl)-acetylarnino]-4-oxo-butyric acid;

4-Dibenzofuran-2-yl-2-[(naphthalene-2-carbonyl)-amino]-4-oxo-butyric acid;

4-Dibenzofuran-2-yl-4-oxo-2-(2-phenoxy-acetylamino)-butyric acid;

4-Dibenzofuran-2-yl-2-(4-methyl-benzoylamino)-4-oxo-butyric acid;

2-[4-(4-Bromo-phenyl)-butyrylamino]-4-dibenzofuran-2-yl-4-oxo-butyric acid;

2-(2-Benzyloxy-acetylamino)-4-dibenzofuran-2-yl-4oxo-butyric acid;

2-(4-Butyl-benzoylamino)-4-dibenzofuran-2-yl-4-oxo-butyric acid;

2-(4-Cyano-benzoylamino)-4-dibenzofuran-2-yl-4-oxo-butyric acid;

2-(4-Butoxy-benzoylamino)-4-dibenzofuran-2-yl-4-oxo-butyric acid;

2-(4-Chloro-benzoylamino)4-dibenzofuran-2-yl-4-oxo-butyric acid;

4-Dibenzofuran-2-yl-4-oxo-2-(2,3,4,5,6-pentafluoro-benzoylamino)-butyric acid;

4-Dibenzofuran-2-yl-2-[(furan-2-carbonyl)-amino]-4-oxo-butyric acid;

2-(4-Bromo-benzoylamino)-4-dibenzofuran-2-yl-4-oxo-butyric acid;

4-Dibenzofuran-2-yl-2-(4-fluoro-benzoylamino)4-oxo-butyric acid;

4-Dibenzofuran-2-yl-2-(4-methoxy-benzoylamino)4-oxo-butyric acid;

4-Dibenzofuran-2-yl-2-(3,4-dimethoxy-benzoylamino)4-oxo-butyric acid; and

4-Dibenzofuran-2-yl-4-oxo-2-(4-trifluoromethyl-benzoylamino)-butyric acid.

17. A compound of claim 7 wherein $R_5$ is

and $R_8$ is $C_1$–$C_{10}$ alkyl or substituted $C_1$–$C_{10}$ alkyl.

18. A compound of claim 17 selected from the group consisting of (S)-4-Dibenzofuran-2-yl-4-oxo-2-(octanoyl-amino)-butyric acid;

(S)-4-Dibenzofuran-2-yl-4-oxo-2-(dodecanoyl-amino)-butyric acid;

4-Dibenzofuran-2-yl-2-diphenylacetylamino-4-oxo-butyric acid;

4-Dibenzofuran-2-yl-2-(2,2-dimethylpentanoylamino)-4-oxo-butyric acid;

4-Dibenzofuran-2-yl-4-oxo-2-(2,2,3,3,4,4,5,5,6,6,7,7,8,8, 8-pentadecafluoro-octanoylamino)-butyric acid;

4-Dibenzofuran-2-yl-4-oxo-2-(2-phenoxypropionylamino)-butyric acid;

4-Dibenzofuran-2-yl-2-heptanoylamino-4-oxo-butyric acid; and

4-Dibenzofuran-2-yl-4-oxo-2-(2-phenylbutyrylamino)-butyric acid.

19. A compound of claim 7 wherein $R_5$ is

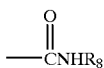
—CNHR$_8$ and $R_8$ is —(CH$_2$)$_{0-6}$-aryl.

20. The compound of claim 19 which is (S)-4-Dibenzofuran-2-yl-2-[3-(2,6-diisopropyl-phenyl)-ureido]-4-oxo-butyric acid.

21. A compound of claim 7 wherein $R_5$ is $S(O)_{1\ or\ 2}$-C$_1$–C$_{20}$ alkyl.

22. The compound of claim 21 which is (S)4-dibenzofuran-2-yl-4-oxo-2-methanesulfonylamino-butyric acid.

23. A compound of claim 7 wherein $R_5$ is $S(O)_{1\ or\ 2}$-aryl.

24. The compound of claim 23 which is (S)-4-dibenzofuran-2-yl-4-oxo-2-(4-methylphenylsulfonylamino)-butyric acid.

25. A compound of claim 7 wherein $R_5$ is

CR$_8$ and $R_8$ is (CH$_2$)$_{0-6}$-(O or S)$_{0-1}$-cycloalkyl.

26. A compound of claim 25 selected from the group consisting of

2-[(Adamantane-1-carbonyl)-amino]-4-dibenzofuan-2-yl-4-oxo-butyric acid;

2-(Cyclopropanecarbonyl-amino)-4-dibenzofuran-2-yl-4-oxo-butyric acid;

2-(Cyclopentanecarbonyl-amino)-4-dibenzofuran-2-yl-4-oxo-butyric acid; and 2-(Cyclohexanecarbonyl-amino)-4-dibenzofuran-2-yl-4-oxo-butyric acid.

27. A compound of claim 7 wherein $R_5$ is

CR$_8$ and $R_8$ is C$_2$–C$_{20}$ alkenyl or substituted C$_2$–C$_{20}$ alkenyl.

28. The compound of claim 27 which is 4-dibenzofuran-2-yl-4-oxo-2-(3-phenyl-acryloylamino)-butyric acid.

29. A compound of claim 5 which is (S)-2-Benzoylamino-4-dibenzofuran-2-yl-4-oxo-butyric acid methyl ester.

30. A compound of claim 3 wherein X is NOR$_9$.

31. A compound of claim 30 which is (S)-4-dibenzofuran-2-yl-4-hydroxyimino-2-(2,2,2-trifluoroacetylamino)-butyric acid.

32. A compound of claim 1 having the formula

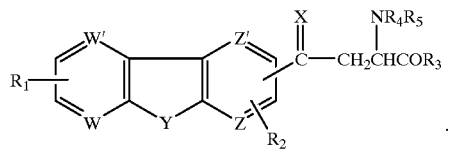

33. A pharmaceutical formulation comprising a compound of claim 1 admixed with a diluent, carrier, or excipient therefor.

34. A method for inhibiting a matrix metalloproteinase enzyme by administering a matrix metalloproteinase inhibiting amount of a compound of claim 1.

35. A method of treating arthritis comprising administering a matrix metalloproteinase inhibiting amount of a compound of claim 1.

36. A method of treating restenosis comprising administering a matrix metalloproteinase inhibiting amount of a compound of claim 1.

37. A method of treating multiple sclerosis comprising administering a matrix metalloproteinase inhibiting amount of a compound of claim 1.

38. A method of treating atherosclerotic plaque rupture comprising administering a matrix metalloproteinase inhibiting amount of a compound of claim 1.

39. A method of treating aortic aneurysms comprising administering a matrix metalloproteinase inhibiting amount of a compound of claim 1.

40. A method of treating heart failure comprising administering a matrix metalloproteinase inhibiting amount of a compound of claim 1.

41. A method of treating periodontal disease comprising administering a matrix metalloproteinase inhibiting amount of a compound of claim 1.

42. A method of promoting wound healing comprising administering a matrix metalloproteinase inhibiting amount of a compound of claim 1.

* * * * *

UNITED STATES PATENT AND TRADEMARK OFFICE
CERTIFICATE OF CORRECTION

PATENT NO. : 6,020,366
DATED : February 1, 2000
INVENTOR(S) : Joseph Armand Picard, et. al.

It is certified that error appears in the above-identified patent and that said Letters Patent is hereby Column 29, line 59 " 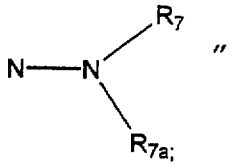 "

should read " 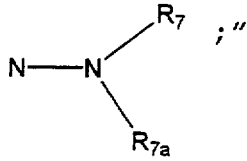 ;"

Column 29, line 61 "$R_{7a}$," should read "$R_{7a}$".

Column 30, line 15 "R" should read "$R_6$".

Column 31, line 10 after the depicted formula insert -- wherein $R_1$, $R_2$, $R_3$, $R_4$, $R_5$, and X are as defined --.

Column 31, line 20 after the depicted formula insert - wherein $R_3$, $R_4$, $R_5$, and X are as defined --.

Column 31, line 64, "benzoylamino4-oxo-butyric" should read "benzoylamino-4-oxo-butyric".

Column 31, line 67, "-acetylarnino" should read "-acetylamino".

Column 32, line 10, "2-yl-4oxo-butyric acid" should read "2-yl-4-oxo-butyric acid"

UNITED STATES PATENT AND TRADEMARK OFFICE
CERTIFICATE OF CORRECTION

PATENT NO. : 6,020,366
DATED : February 1, 2000
INVENTOR(S) : Joseph Armand Picard, et. al.

It is certified that error appears in the above-identified patent and that said Letters Patent is hereby corrected as shown below:

Column 32, line 20, "(4-Chloro-benzoylamino)4-dibenzofuran" should read "(4-Chloro-benzoylamino)-4-dibenzofuran"

Column 32, line 30, "(4-fluoro-benzoylamino)4-oxo" should read "(4-fluoro-benzoylamino)-4-oxo"

Column 32, line 33, "(4-methoxy-benzoylamino)4-oxo" should read "(4-methoxy-benzoylamino)-4-oxo"

Column 32, line 35, "(3,4-dimethoxy-benzoylamino)4-oxo" should read "(3,4-dimethoxy-benzoylamino)-4-oxo"

Column 33, line 13, "(S)4-dibenzofuran" should read "(S)-4-dibenzofuran".
Column 34, line 14, after the depicted formula insert -- wherein $R_3$, $R_4$, $R_5$, W, W', Y, Z, Z', and X are as defined --.

Signed and Sealed this

Twenty-seventh Day of February, 2001

Attest:

NICHOLAS P. GODICI

Attesting Officer      Acting Director of the United States Patent and Trademark Office